ABSTRACT

United States Patent [19]
Wise et al.

[11] 3,935,308
[45] Jan. 27, 1976

[54] WOUND COVERING AND METHOD OF APPLICATION

[75] Inventors: Donald L. Wise, Belmont; Arthur D. Schwope, Watertown, both of Mass.; Kenneth W. Sell, Rockville, Md.

[73] Assignee: The United States of America as represented by the Secretary of the Navy, Washington, D.C.

[22] Filed: Aug. 8, 1974

[21] Appl. No.: 495,705

[52] U.S. Cl. .............. 424/78; 424/45; 424/DIG. 13
[51] Int. Cl.² ........................................ A61K 31/74
[58] Field of Search ................. 424/DIG. 13, 45, 78

[56] References Cited
UNITED STATES PATENTS

| | | |
|---|---|---|
| 2,804,073 | 8/1957 | Gallienne et al............. 424/DIG. 13 |
| 3,021,309 | 2/1963 | Cox et al. .......................... 260/78.3 |
| 3,577,516 | 5/1971 | Gould et al.......................... 424/45 |

OTHER PUBLICATIONS

Chemical Abstracts, Vol. vol 78, (1969), 12318t.

*Primary Examiner*—Frederick E. Waddell
*Attorney, Agent, or Firm*—Richard S. Sciascia; Don D. Doty; Harvey A. David

[57] ABSTRACT

A preparation and a method are described for emergency, interim treatment of extensive burn injuries, e.g., flash burns, to external portions of a person. A solution of the polymer poly-ε-caprolactone is a volatile solvent, such as acetone or tetrahydrofuran, is applied to the burn area by spraying or swabbing, so that upon evaporation of the solvent a film of the polymer is left to serve as a barrier to insensible water loss.

1 Claim, No Drawings

WOUND COVERING AND METHOD OF APPLICATION

STATEMENT OF GOVERNMENT INTEREST

The invention described herein may be manufactured and used by or for the Government of the United States of America for Governmental purposes without the payment of any royalties thereon or therefor.

FIELD OF THE INVENTION

This invention relates to the treatment of burn wounds, and more particularly to a method and means for providing such treatment as a "first aid" expedient, and at times as part of more sophisticated supportive treatment.

Shock is a major cause of death in the immediate period following a severe burn, such as a flash burn, over large portions of the body. A primary cause of shock has been recognized as the excessive loss of body fluids and protein through the burned areas. This loss occurs primarily through evaporation, and the process is not visible or otherwise readily detectable to the subject or observer. The loss is therefore termed insensible, although the results thereof are dramatically apparent in the shock process.

Many, if not most, burn accidents occur under circumstances that make it impossible for the victim to receive immediate supportive treatment in a hospital. Such is the case, for example, with disasters, accidents, or conflicts occurring in remote areas, at sea, or under other adverse conditions. Accordingly, there has long been a need for suitable, adequate, readily available, and easily applied burn treatment that can be administered by relatively unskilled persons at the scene of injury.

DISCUSSION OF THE PRIOR ART

In the past there have been used various creams, greases, sprays, and homemade concoctions designed to sooth and protect the wound, immediately following a burn, as a first-aid treatment. In general, these have been ineffective in stopping insensible fluid and protein loss through the burn site and have been messy and difficult to apply. The latter factors are, of course, deterrents to effective use by unskilled persons in a first-aid situation.

In addition, there have existed various coverings for burns and similar wounds requiring covering of a substantial area for extended periods of time during the skin regeneration and healing process. These have included skin grafts where the skin was obtained either from another person or animal, or from another area of the injured party. Also, there have been provided various sheets, foils, and webs or fabrics made from various synthetic plastic materials, animal collagen, and the like. Examples of the latter are described in U.S. Pat. No. 3,491,760 to Bernhard Braun et al. Use of burn wound coverings in the form of fibrillar products comprising polyglycolic acid are alluded to in U.S. Pat. No. 3,739,773 to Edard E. Schmitt et al. Those burn wound coverings, and particularly those comprising foams, gells or foils of collagen, or other moist, conformable dressing, require special storage techniques and facilities that render them quite impractical to have available for immediate use as a first-aid supply in various remote, isolated, and limited facility places where flash burns and other extensive injuries to the skin may occur.

SUMMARY OF THE INVENTION

The present invention aims to overcome some or many of the disadvantages and shortcomings of the prior art, with respect to emergency or first-aid burn dressings or treatment, through the utilization of our discovery that a thin plastic film of poly-$\epsilon$-caprolactone formed directly on the surface of a burn wound will adhere thereto and will control insensible fluid loss by evaporation so as to occur at a substantially normal rate, and that such a film can be effectively formed by applying a solution of poly-$\epsilon$-caprolactone in a suitable solvent, such as acetone or tetrahydrofuran.

With the foregoing in mind, it is a principal object of the invention to provide an improved wound covering which is suitable for first-aid use on burns, is sufficiently compatible with human tissue and fluids to adhere to a burn wound for a useful period of time, and is notably effective in maintaining fluid balance in a subject.

Another object of the invention is to provide a burn wound treatment materials which can be stored for prolonged periods of time in a convenient and readily usable form, without any requirement for special storage facilities or conditions.

Still another object is the provision of burn treatment material of the foregoing character and comprising poly-$\epsilon$-caprolactone in a solvent or vehicle that will rapidly evaporate after application to a wound surface to leave a thin, covering film of the poly-$\epsilon$-caprolactone adhering to the wound.

As another object, the invention contemplates the packaging of the poly-$\epsilon$-caprolactone and its solvent in a container having means for ejecting the contents thereof in the form of a spray or aerosol onto an affected area to be treated, such as a flash burn.

Yet another object of the invention is to provide a method of burn treatment including the steps of forming a solution of poly-$\epsilon$-caprolactone in a volatile solvent, applying a layer of the solution over a surface to be treated, and allowing the solvent to evaporate so as to form a film of poly-$\epsilon$-caprolactone having a thickness in a predetermined range.

The poly-$\epsilon$-caprolactone, with which the discovery of this invention is concerned, is a biodegradable solid polymer having a molecular weight in the range of 2,000 to 300,000, and which polymer is soluble in liquid solvents, specifically acetone and tetrahydrofuran. U.S. Pat. No. 3,021,309 to E. F. Cox et al describes the polymer poly-$\epsilon$-caprolactone and its generation. The chemical derivation of the polymer per se is not considered to be part of this invention, poly-$\epsilon$-caprolactones having been known in the chemical arts for many years now, as is evident from that patent. Moreover, as also pointed out by that patent, the polymer concerned is soluble in acetone, and is capable of being formed into films.

What is considered to be a notable advancement in the medical art is our discovery that a solution of poly-$\epsilon$-caprolactone in a volatile solvent can be applied directly to a burn wound surface, and that the solvent will evaporate to leave a thin, flexible film or skin of poly-$\epsilon$-caprolactone that will adhere to the wound surface and will effectively control the evaporative water loss from a severe burn during the immediate post burn period and until more conventional supportive burn treatment can be undertaken.

DESCRIPTION OF THE PREFERRED EMBODIMENT

In carrying out the invention it is preferred that the solution of poly-ε-caprolactone be prepared with a solvent that is volatile and substantially non-irritating to a subject when applied thereto. Accordingly, in an exemplary embodiment the solvent may comprise the liquid acetone, and the prepared solution may be placed in a suitable container for prolonged storage in contemplation of possible future emergency use.

In some instances, it may be desirable to utilize a container that has spraying capability, such as the conventional aerosol spray can. A suitable propellant, such as that sold under the name Freon, may be included in a pressurized state in the container to facilitate spraying of the solution. Alternatively, the solution may be stored in a container without spraying capability, with the intention of applying the solution to a burn by means of a swab.

When an injury occurs that removes or destroys the normal water retaining capabilities of a subject's keratinaceous tissue, for example in the case of a severe abrasion, flash burn, or the like, the poly-ε-caprolactone and solvent solution is applied, either by spraying or swabbing, as a coating over the entire injured area. As the solvent evaporates a thin flexible film of the polymer is left adhered to the wound surface. This film, which is preferably in the thickness range of about 0.0005 inch to 0.01 inch in thickness, replaces the destroyed natural keratin moisture barrier. Once the victim reaches a burn treatment center, the film can be removed and traditional burn treatment begun.

Obviously, other embodiments and modifications of the subject invention will readily come to the mind of one skilled in the art having the benefit of the teachings presented in the foregoing description. It is, therefore, to be understood that this invention is not to be limited thereto and that said modifications and embodiments are intended to be included within the scope of the appended claims.

What is claimed is:

1. A method of treating an extensive burn injury to an external portion of a person, comprising the steps of:
   spraying a layer of a solution of poly-ε-caprolactone, having a molecular weight in the range of 2,000 to 300,000, in a volatile solvent comprising liquid tetrahydrofuran onto said external portion;
   allowing said solvent to evaporate so as to leave a thin, flexible film of said poly-ε-caprolactone, having a thickness of about 0.0005 inch to 0.01 inch, adhering to said portion so as to form a barrier to body fluid loss therethrough.

* * * * *